US009365800B2

(12) United States Patent
Harata et al.

(10) Patent No.: US 9,365,800 B2
(45) Date of Patent: Jun. 14, 2016

(54) METHOD FOR PRODUCING COMPOSITION CONTAINING HIGHLY UNSATURATED FATTY ACID ALKYL ESTER

(71) Applicant: NISSHIN PHARMA INC., Chiyoda-ku (JP)

(72) Inventors: Masataka Harata, Ueda (JP); Shirou Fujita, Ueda (JP)

(73) Assignee: NISSHIN PHARMA INC., Chiyoda-ku (JP)

( * ) Notice: Subject to any disclaimer, the term of this patent is extended or adjusted under 35 U.S.C. 154(b) by 0 days.

(21) Appl. No.: 14/432,237

(22) PCT Filed: Sep. 20, 2013

(86) PCT No.: PCT/JP2013/075454
§ 371 (c)(1),
(2) Date: Mar. 30, 2015

(87) PCT Pub. No.: WO2014/054435
PCT Pub. Date: Apr. 10, 2014

(65) Prior Publication Data
US 2015/0252288 A1    Sep. 10, 2015

(30) Foreign Application Priority Data
Oct. 1, 2012  (JP) .................... 2012-219419

(51) Int. Cl.
*C11B 3/00*   (2006.01)
*C11C 1/10*   (2006.01)
(Continued)

(52) U.S. Cl.
CPC ............. *C11B 3/001* (2013.01); *C11C 1/002* (2013.01); *C11C 1/005* (2013.01); *C11C 1/007* (2013.01); *C11C 1/10* (2013.01); *C11C 3/003* (2013.01)

(58) Field of Classification Search
CPC ........ C11B 3/001; C11C 1/002; C11C 1/005; C11C 1/007; C11C 1/10; C11C 3/003
USPC ........................................... 554/184
See application file for complete search history.

(56) References Cited

U.S. PATENT DOCUMENTS 6,200,624 B1    3/2001  Mazer et al.
2012/0083616 A1  4/2012  Harting Glade et al.

FOREIGN PATENT DOCUMENTS

EP    2 438 819    4/2012
JP    06 240289    8/1994
(Continued)

OTHER PUBLICATIONS

International Search Report Issued Dec. 17, 2013 in PCT/JP13/075454 filed Sep. 20, 2013.
(Continued)

*Primary Examiner* — Deborah D Carr
(74) *Attorney, Agent, or Firm* — Oblon, McClelland, Maier & Neustadt, L.L.P

(57) ABSTRACT

The present invention provides a composition having a high content of highly unsaturated fatty acid alkyl ester. A method for producing a composition comprising a highly unsaturated fatty acid alkyl ester, the method comprising contacting a raw material comprising a highly unsaturated fatty acid alkyl ester with an aqueous solution comprising a silver salt and subsequently recovering an aqueous phase; adding an organic solvent to the aqueous phase, and subsequently recovering an organic solvent phase; and rectifying the organic solvent phase at a temperature of 170 to 190° C. and a column top vacuum degree of 1 Pa or less to recover the highly unsaturated fatty acid alkyl ester from the organic solvent phase.

11 Claims, 1 Drawing Sheet

(51) Int. Cl.
*C11C 3/00* (2006.01)
*C11C 1/00* (2006.01)

(56) References Cited

FOREIGN PATENT DOCUMENTS

| JP | 07 242895 | 9/1995 |
| JP | 08 218091 | 8/1996 |
| JP | 09 302380 | 11/1997 |
| JP | 10 095744 | 4/1998 |
| JP | 3005638 | 1/2000 |
| JP | 2000 504221 | 4/2000 |

OTHER PUBLICATIONS

Written Opinion of the International Searching Authority issued Dec. 17, 2013 in PCT/JP13/075454 filed Sep. 20, 2013.
Wijesundera, R.C. et al., "Eicosapentaenoic Acid Geometrical Isomer Artifacts in Heated Fish Oil Esters", Journal of the American Oil Chemists' Society, vol. 66, No. 12, pp. 1822-1830, 1989.

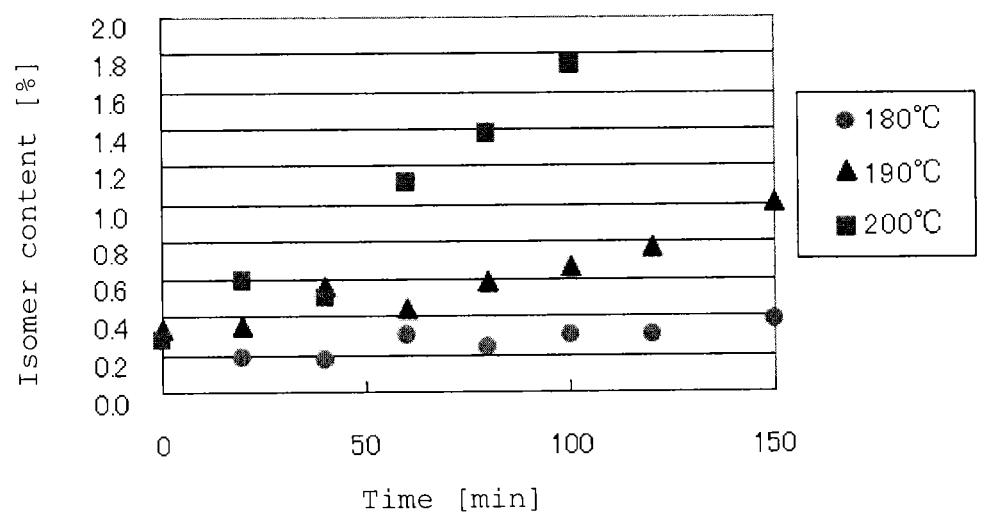

METHOD FOR PRODUCING COMPOSITION CONTAINING HIGHLY UNSATURATED FATTY ACID ALKYL ESTER

This application is a National Stage of PCT/JP13/075454 filed Sep. 20, 2013 and claims the benefit of JP 2012-219419 filed Oct. 1, 2012.

TECHNICAL FIELD

The present invention relates to a method for producing a composition comprising a highly unsaturated fatty acid alkyl ester.

BACKGROUND ART

It was revealed in recent years that highly unsaturated fatty acids such as eicosapentaenoic acid (EPA) and docosahexaenoic acid (DHA) have pharmacological effects, and they are hence used as raw materials for pharmaceutical products and health foods. These highly unsaturated fatty acids have a multiple number of double bonds, whereby being not easily obtainable by chemical synthesis. For this reason, most of the highly unsaturated fatty acids used for industrial applications are produced by extracting or purifying raw materials derived from marine organisms rich in highly unsaturated fatty acids such as fish oils. However, since an organism-derived raw material is a mixture of diverse fatty acids with the different numbers of carbon atoms, the different numbers and positions of double bonds and also component ratios of diastereomers, a content of highly unsaturated fatty acid is not necessarily high. Under such a circumstance, the selective purification of an intended highly unsaturated fatty acid from an organism-derived raw material has been always demanded.

Patent Literature 1 describes a method for purifying a highly unsaturated fatty acid or the alkyl ester thereof by, when treating a raw material containing highly unsaturated fatty acids or alkyl esters thereof by the thin film distillation method, supercritical gas extraction method and urea addition method, carrying out the supercritical gas extraction method later than the thin film distillation method.

Patent Literature 2 describes a method for purifying high purity eicosapentaenoic acid or the lower alcohol ester thereof wherein the method comprises subjecting a raw material containing highly unsaturated fatty acids such as EPA to vacuum rectification and mixing the obtained fraction containing EPA and a lower alcohol ester thereof with an aqueous solution of silver nitrate. The conditions for vacuum rectification are described as a pressure of 5 mmHg (665 Pa) or less, preferably 1 mmHg (133 Pa) or less, and a temperature of 215° C. or less, preferably 210° C. or less.

Further, Patent Literature 3 describes a method for producing eicosapentaenoic acid or the ester thereof in a concentration of 80% or more wherein the method comprises distilling stepwise a raw material containing highly unsaturated fatty acids or the alkyl ester thereof using a 3 or more-stage distillation column. The distillation conditions are described as 10 Torr (1330 Pa) or less, preferably 0.1 Torr (13.3 Pa) or less, and 210° C. or less, preferably 195° C. or less.

However, highly unsaturated fatty acids in a much higher concentration and purity than those obtained by the above conventional methods are demanded as raw materials for pharmaceutical products and health foods.

Highly unsaturated fatty acids exist in a form of cis or trans isomer. Most of the highly unsaturated fatty acids in vivo are the cis isomer but are sometimes converted from the cis isomer to the trans isomer due to heating or the like, during the purification process using an organism-derived raw material (Non Patent Literature 1). Consequently, highly unsaturated fatty acids industrially purified from organism-derived raw materials contain a certain amount of the trans isomer. However, it is reported that trans fatty acid causes health risks, particularly elevates the LDL cholesterol value, and increases the risk of cardiovascular diseases. In the US and Canada, it is obliged to label food products a trans fatty acid content.

Thus, it is demanded to develop, as a raw material for pharmaceutical products and health foods, a composition comprising highly unsaturated fatty acids, which comprises not only an intended highly unsaturated fatty acid in a high concentration but also a trans fatty acid in a reduced content as possible. However, the purification of highly unsaturated fatty acids has never been practiced so far with an attention to the diastereomer ratio.

CITATION LIST

Patent Literature

Patent Literature 1: JP-A-10-95744
Patent Literature 2: JP-A-7-242895
Patent Literature 3: JP-B-3005638

Non Patent Literature

Non Patent Literature 1: Journal of the American Oil Chemists' Society, 1989, 66(12): 1822-1830

SUMMARY OF INVENTION

Technical Problem

The present inventors found that the conventional purification methods of highly unsaturated fatty acids result in an increased content ratio of unpreferable trans isomer when the purification step is repeated to increase the concentration of an intended highly unsaturated fatty acid in a purified product, hence problematic. Then, the present inventors carried out extensive studies with an object of providing a composition comprising highly unsaturated fatty acids in a high concentration and having a low content of the trans isomer of the highly unsaturated fatty acids.

Solution to Problem

As a result, the present inventors have found that when an alkyl ester of a highly unsaturated fatty acid is treated with an aqueous solution containing a silver salt and subsequently subjected to rectification, the production of trans isomer during the purification step of the highly unsaturated fatty acid can be minimized, whereby a composition having a high concentration of the highly unsaturated fatty acid alkyl ester and an extremely low content of the trans isomer is obtained.

More specifically, the present invention provides a method for producing a composition comprising a highly unsaturated fatty acid alkyl ester, the method comprising:

(1) contacting a raw material comprising a highly unsaturated fatty acid alkyl ester with an aqueous solution comprising a silver salt, and subsequently recovering an aqueous phase;

(2) adding an organic solvent to the aqueous phase, and subsequently recovering an organic solvent phase; and (3) rectifying the organic solvent phase at a temperature of 170 to 190° C. and a column top vacuum degree of 1 Pa or less to recover the highly unsaturated fatty acid alkyl ester from the organic solvent phase.

The present invention further provides a composition, which comprises 95 mass % or more of a highly unsaturated fatty acid alkyl ester and in which a trans isomer ratio in the highly unsaturated fatty acid alkyl ester is below 1 mass %.

Advantageous Effects of Invention

According to the present invention, a composition comprising alkyl esters of highly unsaturated fatty acids such as EPA and DHA in high concentrations can be obtained. The composition does not substantially comprise trans fatty acids and is thus useful as a highly unsaturated fatty acid raw material for producing pharmaceutical products and health foods.

BRIEF DESCRIPTION OF DRAWINGS

FIG. 1 Increase of trans fatty acid alkyl ester produced with the increase in rectification temperature.

DESCRIPTION OF EMBODIMENTS

In the method for producing a composition comprising a highly unsaturated fatty acid alkyl ester of the present invention, examples of the intended highly unsaturated fatty acid to be contained in the composition include eicosapentaenoic acid (EPA), arachidonic acid (AA), eicosatetraenoic acid (ETA), docosahexaenoic acid (DHA), docosapentaenoic acid (DPA) and the like, with DHA and EPA being preferable, and EPA being more preferable. Examples of the alkyl group composing the alkyl ester of a highly unsaturated fatty acid include linear or branched chain alkyl groups having 1 to 6 carbon atoms, and the alkyl group is preferably a methyl group or an ethyl group, more preferably an ethyl group.

In the production method of the present invention, the raw materials for the composition comprising a highly unsaturated fatty acid alkyl ester are fats and oils containing an intended highly unsaturated fatty acid. Examples of the raw material include fats and oils derived from marine animals such as fish or plankton, fats and oils derived from microorganisms such as algae, with fats and oils derived from fish such as sardine and yellowtail and fats and oils derived from algae being preferable among them.

The above raw materials are preferably fats and oils containing 40 mass % or more of an intended highly unsaturated fatty acid in the total fatty acid contained therein. The content referred herein is the value in terms of free fatty acids. The intended highly unsaturated fatty acid may be present in a form of free fatty acid in the raw material, or may be present in a form of a fatty acid of mono-, di- or triglyceride. In the production method of the present invention, when a raw material having a content of the intended highly unsaturated fatty acid of 40 mass % or more in the total fatty acid contained is used, a composition having a concentration of 95 mass % or more, preferably 96 mass % or more, more preferably 98 mass % or more, of the intended highly unsaturated fatty acids can be efficiently obtained in the end.

Further, in the above raw materials, the trans isomer ratio in an intended highly unsaturated fatty acid (the ratio of trans isomer amount to the total amount of the intended highly unsaturated fatty acid) is preferably below 3 mass %, more preferably below 2 mass %. In the production method of the present invention, when a raw material in which a trans isomer ratio in an intended highly unsaturated fatty acid is below 3% is used, a composition in which a trans isomer ratio in the intended highly unsaturated fatty acid is below 1 mass %, preferably 0.5 mass %, can be efficiently obtained in the end.

In the production method of the present invention, the intended highly unsaturated fatty acid in the raw material is alkyl-esterified. Alkyl esterification can prevent the highly unsaturated fatty acid from being trans isomerized during the production process of the composition of the present invention. The highly unsaturated fatty acid alkyl ester can be produced by an esterification reaction of fats and oils containing highly unsaturated fatty acids and an acid having a desired alkyl group through a known method. For example, an alkyl-esterified product of a highly unsaturated fatty acid can be obtained easily by saponifying fats and oils containing triglyceride of the highly unsaturated fatty acid. The higher degree of alkyl esterification is preferable, and preferably 90% or more, more preferably 95% or more, of an intended highly unsaturated fatty acids (including free fatty acid) contained in the raw material is alkyl-esterified.

For the oils and fats containing the above highly unsaturated fatty acid and an alkyl ester thereof, commercially available fats and oils may be used. From the viewpoint of the object of the present invention described above, specifically, obtaining a high content of an intended highly unsaturated fatty acid or an alkyl ester thereof, it is preferable to use commercially available fats and oils derived from fish oils which have the standardized kind and amount of highly unsaturated fatty acids.

In each step of the method for producing the composition comprising a highly unsaturated fatty acid alkyl ester of the present invention, it is preferable that the above raw material be applied in a form of liquid. When the raw material is in a form of liquid at the reaction temperature in each step, the raw material can be used directly in each step of the present invention. When the raw material is in a form of solid at the reaction temperature in each step, the raw material is dissolved in or diluted with a suitable organic solvent or other oils for use. For the organic solvents, an organic solvent separable from water are used to carry out the following step (1), and examples thereof include ethyl acetate, chloroform, carbon tetrachloride, diethyl ether, hexane and the like.

The method for producing a composition comprising a highly unsaturated fatty acid alkyl ester of the present invention is carried out as follows:

(1) contacting a raw material comprising a highly unsaturated fatty acid alkyl ester with an aqueous solution comprising a silver salt, and subsequently recovering an aqueous phase;

(2) adding an organic solvent to the aqueous phase, and subsequently recovering an organic solvent phase; and (3) rectifying the organic solvent phase to recover the highly unsaturated fatty acid alkyl ester from the organic solvent phase.

The production steps (1) and (2) of the present invention adopt purification techniques which take advantage of changing solubility in an extraction solvent when a silver salt forms a complex at the double bond on the highly unsaturated fatty acid, and are the steps in which the highly unsaturated fatty acid alkyl ester is separated and purified. More specifically, the efficient separation and purification can be achieved for a highly unsaturated fatty acid having 20 or more carbon atoms such as the alkyl ester of eicosapentaenoic acid (EPA), arachidonic acid (AA), eicosatetraenoic acid (ETA), docosahexaenoic acid (DHA), or docosapentaenoic acid (DPA).

The step (1) of the production method of the present invention is a step of contacting a raw material containing a highly unsaturated fatty acid alkyl ester with an aqueous solution containing a silver salt and subsequently recovering the aqueous phase. This step is carried out in accordance with the methods described in JP-B-2786748, JP-B-2895258, JP-B-2935555, JP-B-3001954 and the like.

More specifically, an aqueous solution containing a silver salt is added to the raw material containing an intended highly unsaturated fatty acid alkyl ester described above and the mixture is stirred for about 5 minutes to 4 hours, preferably about 10 minutes to 2 hours. The upper limit of the reaction temperature at this procedure is preferably the temperature at which the resulting product of the step (1) is completely liquefied, e.g., about 80° C. or less, whereas the lower limit is 5° C. or more. The reaction temperature is more preferably close to room temperature (20 to 30° C.). The reaction forms a silver-highly unsaturated fatty acid complex. As the thus formed complex is dissolved in the aqueous solution phase, the intended highly unsaturated fatty acid can be selectively recovered by recovering the aqueous phase from the solution.

The silver salt is not limited as long as it can form a complex with an unsaturated bond of the highly unsaturated fatty acid, and silver nitrate, silver perchlorate, silver tetrafluoroborate, silver acetate or the like, can be used. Of these, silver nitrate is preferable. Examples of the solvent for aqueous solution include water, mixed media of water and a compound having a hydroxy group such as glycerol or ethylene glycol, but water is preferably used. The silver salt concentration in the aqueous solution may be 0.1 mol/L or more, preferably about 1 to 20 mol/L. The molar ratio of a highly unsaturated fatty acid to a silver salt is about 1:100 to 100:1, preferably about 1:5 to 1:1.

The step (2) of the production method of the present invention is a step of adding an organic solvent to the aqueous phase recovered in the above step (1), and the extracting highly unsaturated fatty acid alkyl ester in the aqueous phase with the organic solvent phase, followed by recovering the organic solvent phase containing the highly unsaturated fatty acid alkyl ester. This step is carried out in accordance with the methods described in JP-B-2786748, JP-B-2895258, JP-B-2935555, JP-B-3001954 and the like.

Examples of the organic solvent added to the aqueous phase include hexane, ether, ethyl acetate, butyl acetate, chloroform, cyclohexane, benzene, toluene, xylene and the like, which highly dissolves the highly unsaturated fatty acid and are separable from water. Preferably, the solution (reaction solution) to which the organic solvent has been added is heated to a temperature higher than the reaction temperature in the above step (1), more specifically higher than the temperature at which the above silver-highly unsaturated fatty acid complex is formed. More preferably, the reaction solution is heated to a temperature higher by at least 20° C. than the reaction temperature in the step (1), more specifically, a temperature higher by at least 20° C. than the temperature at which the complex is formed. For example, when the complex is formed at room temperature in the step (1), the temperature of reaction solution in the step (2) is preferably about 40° C. or higher, more preferably about 50 to 80° C. The extraction reaction time of the highly unsaturated fatty acid alkyl ester into the organic solvent phase is desirably 10 minutes to 6 hours, preferably 30 minutes to 2 hours, and the solution is desirably stirred during the reaction. Subsequently, the aqueous phase is removed and the organic solvent phase containing the highly unsaturated fatty acid alkyl ester is recovered. Further, the recovered organic solvent phase is allowed to pass through an adsorbent such as silica gel, activated carbon or silicon dioxide to further remove the residual silver ion.

The step (3) of the production method of the present invention is a step of rectifying the organic solvent phase obtained in the step (2) to recover an intended highly unsaturated fatty acid alkyl ester. In more detail, the intended highly unsaturated fatty acid ester is selectively recovered from the organic solvent phase containing the highly unsaturated fatty acid alkyl ester obtained in the step (2) by use of the difference in boiling points.

For the rectification in the step (3), vacuum rectifiers adopting the known system such as packing-, spring- or trays-type, can be used, or alternatively the continuous distillation system may be employed. However, the conditions for rectification are set lower pressure and temperature, as compared with those of the conventional rectification method. More specifically, in the method of the present invention, the conditions for the rectification in the step (3) are a column top vacuum degree of a rectifier of 1 Pa or less, preferably 0.5 Pa or less, and a rectification temperature of 170 to 190° C., preferably 180 to 185° C. When a column top vacuum degree exceeds 1 Pa, the trans isomer of a highly unsaturated fatty acid is likely to be produced. When a rectification temperature is below 170° C., the yield of an intended highly unsaturated fatty acid is reduced. On the other hand, when a rectification temperature exceeds 190° C., the trans isomer of a highly unsaturated fatty acid is likely to be produced. The rectification temperature in this step refers to a temperature of the organic solvent phase containing the highly unsaturated fatty acid alkyl ester.

The fraction containing the highly unsaturated fatty acid alkyl ester obtained in the above rectification step may be refluxed and subjected again to the rectification under the above conditions.

In the method for producing a composition comprising the highly unsaturated fatty acid alkyl ester of the present invention, each of the above steps (1), (2) and (3) is carried out in the order as indicated. When this order is not followed, it is not possible to obtain a composition comprising an intended highly unsaturated fatty acid in a high content in which a trans isomer ratio in the intended highly unsaturated fatty acid is sufficiently low. Particularly, when the step (3) is carried out before the step (1) or (2), a composition comprising an intended highly unsaturated fatty acid in a high content is difficulty obtained or a composition comprising an intended highly unsaturated fatty acid in a high content but having a high trans isomer ratio is obtained.

The composition comprising a highly unsaturated fatty acid alkyl ester produced by the production method of the present invention comprises 95 mass % or more, preferably 96 mass % or more, more preferably 98 mass % or more, of the intended highly unsaturated fatty acid alkyl ester in the total fatty acid contained, in terms of free fatty acid. The intended highly unsaturated fatty acid alkyl ester contained in the composition is preferably the alkyl ester of DHA or the alkyl ester of EPA, with the alkyl ester of EPA being more preferable. Further, the trans isomer ratio in an intended highly unsaturated fatty acid alkyl ester contained in the composition is below 1 mass %, preferably below 0.5 mass %.

EXAMPLES

Hereinafter, the present invention is further described in details with reference to Examples, but is not limited thereto.

In the following Examples, the composition analysis method of highly unsaturated fatty acids and the quantitative method of diastereomers are as follows.

9 µL of a test sample to be measured was diluted in 1.5 mL of n-hexane and analyzed for the content ratio of each fatty acid and the content ratio of isomer under the following conditions using a gas chromatography equipment (Type 6890 GC; manufactured by Agilent Technologies). The results were obtained by the conversion from the chromatogram area, expressed in mass %.

<Column Conditions>

Column: DB-WAX, manufactured by J&W Scientific, inc, 0.25 mm×30 m, column temperature: 210° C.

He flow rate: 1.0 ml/min, He pressure: 134 kPa

<Detection Conditions>

$H_2$ flow rate: 30 ml/min, Air flow rate: 400 ml/min

He flow rate: 10 ml/min, detection temperature: 260° C.

The isomer ratio in an intended highly unsaturated fatty acid was determined by the following formula.

$$\text{Ratio of isomer (cis isomer or trans isomer) in an intended fatty acid} = \frac{[\text{Content ratio of the intended fatty acid isomer (cis isomer or trans isomer) in the composition}]}{[\text{Content ratio of the intended fatty acid (cis isomer + trans isomer) in the composition}]}$$

Example 1

Raw material: 1000 mL of an absolute ethanol solution in which 50 g of sodium hydroxide was dissolved was added to 1 kg of sardine oil, and the resultant was mixed with stirring at 70 to 80° C. for 1 hour. 500 mL of water was further added thereto and mixed thoroughly, and the mixture was allowed to stand still for 1 hour. The separated aqueous phase was removed and the oil phase was washed with water several times, followed by neutralizing the washings to obtain 820 g of ethyl esterified sardine oil.

As shown in Table 1, the above sardine oil contained eicosapentaenoic acid (EPA) 44.09% (mass %, hereinafter referred to the same), eicosatetraenoic acid (ETA) 1.52%, arachidonic acid (AA) 1.77% and docosahexaenoic acid (DHA) 6.92% based on the total fatty acid. The trans isomer ratio in EPA was 1.23%.

Step (1): 160 mL of n-hexane was added to 300 g of the ethyl esterified sardine oil prepared above, and mixed with stirring for dissolution. 500 mL of an aqueous solution of 50 mass % silver nitrate was added thereto and stirred under the condition of 5 to 30° C. After allowing the mixture to stand still, the separated n-hexane phase was removed and the aqueous phase was recovered.

Step (2): 2000 mL of fresh n-hexane was added to the aqueous phase obtained in the step (1), and stirred thoroughly at 50 to 69° C. to extract the fatty acid ethyl ester into n-hexane. After allowing the mixture to stand still, the separated aqueous phase was removed and the n-hexane phase was concentrated. As shown in Table 1, the roughly purified product of fatty acid ethyl ester contained in the n-hexane phase contained EPA 74.54%, ETA 0.32%, AA 0.17% and DHA 14.87% based on the total fatty acid. The trans isomer ratio in EPA was 0.19%.

Step (3): the n-hexane phase containing the fatty acid ethyl ester obtained in the step (2) was subjected to rectification using a column packing rectifier while maintaining the conditions of a column top vacuum degree of 1 Pa or less and a rectification temperature of 170 to 190° C., whereby obtaining a composition comprising a highly purified EPA ethyl ester in a yield of about 60%. As shown in Table 1, the thus obtained EPA ethyl ester-containing composition contained EPA 98.25%, ETA 0.43%, AA 0.21% and DHA 0.05% in the total fatty acid. The trans isomer ratio in EPA was 0.45%.

The yield of EPA in the present Example, in which the steps were carried out in the order of (1), (2) and (3), was about 53%.

Example 2

An EPA ethyl ester-containing composition was obtained in a yield of about 58% in the same manner as in Example 1 in which the steps were carried out in the order of (1), (2) and (3), except that the step (3) was carried out while maintaining the rectification temperature condition of 180 to 185° C. As shown in Table 1, the thus obtained EPA ethyl ester-containing composition contained EPA 98.29%, ETA 0.40%, AA 0.32% and DHA 0.05% in the total fatty acid. The trans isomer ratio in EPA was 0.28%, which was extremely low.

Comparative Example 1

An EPA ethyl ester containing-composition was obtained in the same manner as in Example 1, except that a column top vacuum degree was 13.3 Pa (0.1 Torr) in the step (3). As shown in Table 1, the thus obtained composition had a high EPA content ratio of 97.44% in the total fatty acid, but the trans isomer ratio in EPA was high (1.37%).

Comparative Example 2

The rectification (step (3)) of the ethyl esterified sardine oil was carried out first and subsequently the steps (1) and (2) were carried out to obtain an EPA ethyl ester-containing composition. Each of the steps had the same conditions as in Example 1. As shown in Table 1, the thus obtained composition contained EPA 95.05%, ETA 0.72%, AA 0.50% and DHA 0.21% in the total fatty acid, and the trans isomer ratio in EPA was 1.55%. The yield of EPA in the present Comparative Example, in which the steps were carried out in the order of (3), (1) and (2), was about 31%, significantly reducing the EPA yield compared with Example 1.

The EPA content in the total fatty acid in the composition was increased to 98.12% by changing the conditions of rectification (0.5 Pa, 185 to 195° C.) in the present Comparative Example. But the yield was further reduced and the trans isomer ratio in EPA was 2.01%, resulting in a further increase.

TABLE 1

| Mass % | Raw material | Example 1 Product obtained after step (2) | Example 1 Final product | Example 2 Final product | Comparative Example 1 Final product | Comparative Example 2 Final product |
|---|---|---|---|---|---|---|
| Arachidonic acid (AA) | 1.77 | 0.17 | 0.21 | 0.32 | 0.63 | 0.50 |
| Eicosatetraenoic acid (ETA) | 1.52 | 0.32 | 0.43 | 0.40 | 0.86 | 0.72 |
| Docosahexaenoic acid (DHA) | 6.92 | 14.87 | 0.05 | 0.05 | 0.22 | 0.21 |

TABLE 1-continued

| Mass % | Example 1 Raw material | Example 1 Product obtained after step (2) | Example 1 Final product | Example 2 Final product | Comparative Example 1 Final product | Comparative Example 2 Final product |
|---|---|---|---|---|---|---|
| Eicosapentaenoic acid (EPA) | 44.09 | 74.54 | 98.25 | 98.29 | 97.44 | 95.05 |
| Eicosapentaenoic acid (cis isomer ratio) | 98.77 | 99.81 | 99.55 | 99.72 | 98.63 | 98.45 |
| Eicosapentaenoic acid (trans isomer ratio) | 1.23 | 0.19 | 0.45 | 0.28 | 1.37 | 1.55 |
| Eicosapentaenoic acid yield | — | — | 52.9% | 58.1% | 51.0% | 30.8% |

Examples 3 and 4, Comparative Example 3

Highly purified EPA ethyl ester-containing compositions were obtained and the trans isomer ratios in EPA in the compositions were determined in the same manner as in Example 1, except that in the step (3) the rectification temperatures were 180° C. (Example 3), 190° C. (Example 4) and 200° C. (Comparative Example 3) and the rectification time was changed to various times. The results are shown in FIG. 1. FIG. 1 reveals that the trans isomer ratios were below 1 mass % in Examples 3 and 4, in which the rectification temperatures were 190° C. or less, whereas the trans isomer ratio exceeds 1 mass % after one-hour rectification in Comparative Example 3, in which the rectification temperature was 200° C.

The invention claimed is:

1. A method for producing a composition comprising a highly unsaturated fatty acid alkyl ester, the method comprising:
   (1) contacting a raw material comprising a highly unsaturated fatty acid alkyl ester with an aqueous solution comprising a silver salt, and subsequently recovering an aqueous phase;
   (2) adding an organic solvent to the aqueous phase, and subsequently recovering an organic solvent phase; and
   (3) rectifying the organic solvent phase at a temperature of 170 to 190° C. and a column top vacuum degree of 1 Pa or less to recover the highly unsaturated fatty acid alkyl ester from the organic solvent phase.

2. The method according to claim 1, wherein the raw material comprises 40 mass % or more of the highly unsaturated fatty acid in the total fatty acid comprised therein and a trans isomer ratio in the highly unsaturated fatty acid is below 3 mass %.

3. The method according to claim 1, wherein the rectification is carried out under a condition of a column top vacuum degree of 0.5 Pa or less.

4. The method according to claim 1, wherein the rectification is carried out under a condition of 180 to 185° C.

5. The method according to claim 1, wherein, in the step (2), the reaction solution is heated to a temperature higher by at least 20° C. than the reaction temperature in the step (1).

6. The method according to claim 1, wherein the highly unsaturated fatty acid is eicosapentaenoic acid or docosahexaenoic acid.

7. The method according to claim 6, wherein the highly unsaturated fatty acid is eicosapentaenoic acid.

8. A composition comprising 95 mass % or more of a highly unsaturated fatty acid alkyl ester in the total fatty acid, wherein a trans isomer ratio in the highly unsaturated fatty acid alkyl ester is below 1 mass %.

9. The composition according to claim 8, wherein the highly unsaturated fatty acid alkyl ester is an alkyl ester of eicosapentaenoic acid or docosahexaenoic acid.

10. The composition according to claim 9, wherein the alkyl ester of the highly unsaturated fatty acid alkyl ester is an alkyl ester of eicosapentaenoic acid.

11. The method according to claim 1, comprising a single rectifying step.

* * * * *